United States Patent [19]

Yosuke et al.

[11] Patent Number: 5,346,542
[45] Date of Patent: Sep. 13, 1994

[54] AQUEOUS DISPERSION OF ENTERIC POLYMERS AND A METHOD FOR PRODUCING THE SAME

[75] Inventors: Honda Yosuke; Tanabe Tsuneaki; Yaginuma Yoshihito, all of Nobeoka, Japan

[73] Assignee: Asahi Kasei Kogyo Kabushiki Kaisha, Osaka, Japan

[21] Appl. No.: 973,125

[22] Filed: Nov. 6, 1992

[30] Foreign Application Priority Data

Nov. 6, 1991 [JP] Japan ................................. 3-289957

[51] Int. Cl.$^5$ ............................................... C08L 1/08
[52] U.S. Cl. ..................... 106/194; 106/170; 106/197.1; 106/197.2; 106/198; 514/57; 536/84; 536/85; 536/87; 536/97; 536/98
[58] Field of Search ............... 106/170, 194, 197.1, 106/197.2, 198; 536/84, 97, 98, 85, 87; 514/57

[56] References Cited

U.S. PATENT DOCUMENTS

| | | | |
|---|---|---|---|
| 4,177,177 | 12/1979 | Vanderhoff et al. | 106/170 |
| 4,287,221 | 9/1981 | Tonedachi et al. | 427/3 |
| 4,385,078 | 5/1983 | Onda et al. | 106/170 |
| 4,462,839 | 7/1984 | McGinley et al. | 106/198 |
| 4,502,888 | 3/1985 | Leng et al. | 106/194 |
| 4,520,172 | 5/1985 | Lehmann et al. | 525/369 |
| 4,606,771 | 8/1986 | Mukohyama et al. | 106/170 |
| 4,650,716 | 3/1987 | Gelman | 106/197.2 |
| 4,960,814 | 10/1990 | Wu et al. | 106/197.2 |
| 5,025,004 | 6/1991 | Wu et al. | 106/194 |
| 5,028,263 | 7/1991 | Burdick | 106/194 |
| 5,194,464 | 3/1993 | Itoh et al. | 106/198 |

FOREIGN PATENT DOCUMENTS

| | | |
|---|---|---|
| 0135829 | 4/1985 | European Pat. Off. . |
| 0352800 | 1/1990 | European Pat. Off. . |
| 59-193832 | 11/1984 | Japan . |
| 61-207342 | 9/1986 | Japan . |
| 1393374 | 5/1975 | United Kingdom . |

OTHER PUBLICATIONS

European Search Report on European Patent Application No. 92310127.3 no date.
Patent Abstracts of Japan, C filed, vol. 9, No. 52, p. 160 C269 no date.
Patent Abstracts of Japan, C filed, vol. 9, No. 180, p. 126 C 293 no date.

*Primary Examiner*—Anthony Green
*Attorney, Agent, or Firm*—Pennie & Edmonds

[57] ABSTRACT

A novel polymer aqueous dispersion of enteric cellulose derivatives without ester bonded substituents, of which anionic functional groups form salts with cations. The aqueous dispersion of the present invention is used as coating agents for foods and pharmaceuticals. It has high dispersion stability such as high mechanical stability and high storage stability.

9 Claims, No Drawings

AQUEOUS DISPERSION OF ENTERIC POLYMERS AND A METHOD FOR PRODUCING THE SAME

BACKGROUND OF THE INVENTION

1. Field of the Invention

The present invention relates to an aqueous dispersion of enteric cellulose derivatives without ester-bonded substituents, of which anionic functional groups form salts with cations. The aqueous dispersion of the present invention, which can be used as coating agents for foods and pharmaceuticals, has high dispersion stability such as high mechanical stability and high storage stability. Also, the present invention relates to a method for producing the above aqueous dispersion.

2. Description of the Related Art

Various polymers having anionic functional groups are widely used in the field of fibers and textiles, paper making, feed, foods, cosmetics, pharmaceuticals and agricultural chemicals, painting, housing materials, oil mining, ceramics, and the like. They are especially useful as an enteric material for coating use in the field of pharmaceuticals.

For pharmaceutical use, coating agents in an organic solvent phase are gradually being replaced by those in an aqueous phase, because of the remaining organic solvent in pharmaceuticals, high cost of organic solvents and unfavorable working conditions. Several known coating methods in the aqueous phase are listed as follows:

1) A method wherein polymers are dissolved in an aqueous liquid medium.
2) A method wherein fine particles of water-insoluble polymers are dispersed in water.
3) A method wherein latex-type aqueous dispersions of polymers are used.

With method 1), it is well known that the water-soluble polymers like hydroxypropyl methyl cellulose are dissolved in purified water, then the solution is applied as a film coating so as to mask the taste of medicines and improve the impact-strength of pharmaceuticals. With method 2), it is suggested that the fine particles of carboxymethyl ethyl cellulose or hydroxypropyl methyl cellulose phthalate are directly dispersed in water (U.S. Pat. No. 4,287,221). Also, it is suggested that the fine particles of carboxymethyl ethyl cellulose are dispersed in alcohol aqueous solutions with plasticizers, surfactants, emulsifiers and the like (U.S. Pat. No. 4,606,771). It is also suggested that the fine particles of carboxymethyl ethyl cellulose are dispersed in water and 0.5-15% of the cellulose are neutralized, and then the resulting products are applied as a film coating (Japanese Patent laid-open No. 59-193832).

With method 3) where the latex-type aqueous dispersion of enteric acrylic copolymers is used, it is known that various monomers having carboxyl groups are polymerized by the method of emulsion polymerization, then the polymeric dispersion is applied as a film coating. (British Patent No. 1,393,374). Also, it is known that dried acrylic enteric latex particles having functional groups capable of forming salts can be dispersed in water with agents which can form salts, and then the dispersion can be applied as a film coating. With method 3) where the latex-type aqueous dispersion of the polymers other than acrylic copolymers is used, it is suggested that the cellulose polymers can be dispersed to form the latex by the emulsion-solvent evaporation method (U.S. Pat. No. 4,177,177). Also, it is suggested that the latex of cellulose acetate phthalate made by this method is spray dried with re-dispersion agents to get the enteric film agent having improved storage stability.

However, in method 1), necessary properties like enteric properties cannot be obtained because the polymers must be dissolved in water or aqueous medium. In method 2), the suspension must be stirred continuously because of low suspension stability. Also, its film-forming property is not satisfactory because the size of the particles is large and their shape is irregular.

In the latex type aqueous dispersion of the enteric polymers which are based on the acrylic copolymers, it is difficult to completely remove the remaining monomers. Also, the dispersion is likely to change in quality according to the temperature and the shearing stress placed on it, because of properties of acrylic copolymers. Such properties are not desirable when the dispersion is used as a film coating material for pharmaceutical products. Other than the acrylic copolymers, cellulose acetate phthalate can be used to produce the latex, however, it is not an appropriate material for the aqueous dispersion because of its hydrolytic tendencies and poor storage stability. Other enteric coating agents which have ester-bonded substituents such as hydroxypropyl methyl cellulose phthalate, also exhibit poor storage stability.

Therefore, an object of the present invention is to provide an aqueous dispersion of enteric polymers, which has high dispersion stability such as high mechanical stability and high storage stability due to the dispersed particles having self-emulsion properties.

Another object is to provide a novel method for preparing the aqueous dispersion which has the above properties.

These and other objects of the invention as well as the advantages thereof can be had by reference to the following description and claims.

SUMMARY OF THE INVENTION

The present inventors have made extensive and intensive studies relating to the latex-type coating agents in order to solve the above problems, which solution is the subject matter of the present invention.

The present invention provides a novel aqueous dispersion of enteric cellulose derivatives without ester-bonded substituents, wherein the cellulose derivatives have anionic functional groups, part of which is forming nontoxic salts. Such dispersions possess the above-identified properties.

The present invention also provides a novel method for producing the above aqueous dispersions.

DETAILED DESCRIPTION OF THE INVENTION

In one aspect of the present invention, there is provided a novel aqueous dispersion of enteric polymers comprising water and enteric cellulose derivatives without ester-bonded substituents, wherein the cellulose derivatives have anionic functional groups, part of which is forming nontoxic salts.

In another aspect of the present invention, there is provided a method for producing an aqueous dispersion of enteric polymers, which comprises the following steps of:

i) dissolving enteric cellulose derivatives without ester-bonded substituents in an organic solvent which is substantially water immiscible, ii) dispersing the solution with water in the presence of alkalies to form nontoxic salts with the anionic functional groups of the cellulose derivatives, and iii) removing the organic solvent from the dispersion.

The enteric cellulose derivatives of the present invention have anionic functional groups possessing enteric properties. Also, the enteric cellulose derivatives of the present invention are the cellulose derivatives into which anionic functional groups and other functional groups are introduced through any type of chemical bonds except ester-bonds, because the aqueous dispersion must be hydrolytically stable under normal preservative conditions. Therefore, the cellulose derivatives of the present invention includes the etherified cellulose derivatives formed by reaction of alkyl halides, dialkyl sulfuric acids, alkylene oxides, vinyl compounds and the like, the grafted cellulose derivatives formed by chain transfer reactions, the direct oxidation method, the peroxidation method and the like, and the deoxidated cellulose derivatives formed by nucleophilic substitution reactions such as the chloro deoxidated, aminodeoxidated and cyanodeoxidated cellulose derivatives. These cellulose derivatives must at the same time be enteric. As used herein, the term "enteric" means that the material is insoluble in gastric juice (pH=1~3.5) but soluble in intestinal juice (pH 6~7).

The inorganic esterified cellulose derivatives formed by reaction of nitric acids, sulfuric acids, sulfur trioxides and the like, the organic esterified cellulose derivatives formed by reaction of organic acid chlorides, organic acid anhydrides and the like and carbamated cellulose derivatives formed by reaction of isocyanates are not included in the present invention, even if they are enteric. Such cellulose derivatives are not applicable to the present invention, because their functional groups are decomposed by hydrolysis.

Representative examples of the enteric cellulose derivatives of the present invention are carboxymethyl ethyl cellulose, carboxyethyl methyl cellulose, carboxybutyl ethyl cellulose, carboxymethyl cellulose and mixtures thereof. Any polymers without ionic function groups like ethyl cellulose and acrylic polymers can be mixed with the above cellulose derivatives.

In the present invention, the organic solvent in which the enteric cellulose derivatives are dissolved must be substantially water immiscible. The substantially water immiscible organic solvent includes completely water immiscible solvents and solvents which can not be freely miscible with water but can be dissolved in water in small amounts and can dissolve water in small amounts. For the latter solvent, it may contain water at the saturated concentration or below.

Substantially water immiscible solvents may be hydrocarbons such as toluene and cyclohexane, ethers such as isopropyl ether, ketones such as methyl ethyl ketone, halogenated hydrocarbons such as chloroform and methylene chloride, esters such as methyl acetate, ethyl acetate, propyl acetate, isopropyl acetate, methyl formate, ethyl formate and propyl formate and mixtures thereof. It is preferred that the solvent has a boiling point lower than that of water, especially below 90° C., because the organic solvent must be evaporated in the later steps of the procedure. The ketones such as methyl ethyl ketone are more preferable, because of their unhydrolytic properties. Further, small amounts of ethanol, tetrahydrofuran and acetone may be added to the solvent to improve the solubility of the enteric cellulose derivatives.

The ratio of the dissolved cellulose derivatives in the solvent is optionally selected and may be determined according to productivities, handling of the solution and dispersion properties with water. The preferable concentration depends upon the kind of enteric cellulose derivatives being used, the molecular weight thereof and the kind of solvent being used. The concentration is typically between about 1 and 30%, preferably between 4 and 20%.

In the present invention, the term "water" means water itself and water in which an organic solvent, which is soluble in water in small amounts such as methylethyl ketone, methyl acetate and ethyl acetate, is dissolved.

The percentage of the solution of cellulose derivatives which are dispersed in water is determined by the concentration of the cellulose derivatives in the solution and that of the desired latex solids. For example, if the concentration of the cellulose derivatives is 10 weight % based on the solution and that of the desired latex solids is 20 weight %, the ratio of the solution and water can be set as 10:4. It may be possible that more water is used and the obtained low concentration latex is concentrated up to the desired solids concentration by removing water by distillation, membrane separation and the like.

Regarding the alkalies used in the present invention, it is desirable that the alkalies are divalent ions or trivalent ions in water. Also, the alkalies of the present invention shall be nontoxic when the enteric latex is formed. Representative examples of the alkalies are calcium hydroxide, magnesium hydroxide, aluminum hydroxide and barium hydroxide. Monovalent alkalies cannot be applied to the present invention, because if they are used, the obtained latex exhibits very high viscosity compared with the latex formed by the divalent or trivalent alkalies. The divalent alkalies are more desirable due to the high stability and the proper viscosity of the latex formed by the divalent alkalies.

In the present invention, the term "nontoxicity" means extremely low acute toxicity, subacute toxicity and chronic toxicity against the human body and no adverse effects on reproduction.

The alkali shall be added in an amount that part of the anionic functional groups of the cellulose derivatives is neutralized. The ratio of the neutralization may be determined according to the kind of cellulose derivatives being used including the kind of the substituents present, the degree of substitution and the degree of polymerization. When carboxymethyl ethyl cellulose is used, it is usually desirable that from 0.5 to 30 mol % of the carboxymethyl ethyl groups is neutralized. It is generally desirable that from 0.5 to 60 mol % of the anionic functional groups is neutralized regardless of the kind of cellulose derivatives being used. If the alkali is used in excess, the cellulose derivatives tend to be water-soluble so that they are not emulsified or the obtained aqueous dispersion sets to a gel on standing, which is not practicable. On the other hand, if too little alkali is added, the aqueous phase and the oil phase separate from each other, because the dispersion with the solvent is unstable. Even if the aqueous dispersion can be obtained, it separates from water because the size of the dispersed particles is too large to be a stable dispersion.

It has been very difficult heretofore to make the latex of polymers by the emulsion-solvent evaporation method without using emulsifiers. However, it becomes possible to make the latex type aqueous dispersion by using the alkalies in an amount taught by the present invention. The alkali can be added either to the mixtures of the cellulose derivative solution and water, to the cellulose derivative solution or to water. It is preferable that the alkali is added to water to avoid local neutralization.

For the purpose of further improving physical properties of the enteric latex and the coating film and making the process easy, additives such as a plasticizer, an anti-foaming agent and a suspension agent can be added during the step of the dispersion procedure or to the manufactured enteric latex. Representative examples of the plasticizer are diacetin, triacetin, olive oil, peanut oil, castor oil, hard fats, glycerine, glycerides, acetyl monoglycerides, butylphthalyl butyl glycolate, polyethylene glycol, propylene glycol, citric acid esters, sucrose fatty acids esters, middle-chain fatty acids esters, fatty acids esters, sebacic acid esters, phthalic acid esters, cetanol and D-sorbitol. Representative examples of the anti-foaming agent are silicone resin emulsions, silicone anti-foaming agents and dimethyl polysiloxanes. Representative examples of the suspension agent are sodium alginate, carboxymethyl cellulose, hydroxypropyl cellulose, hydroxypropyl methyl cellulose, polyvinyl alcohol, polyvinyl pyrolidone, polyethylene glycol and methyl cellulose. These additives can be used separately and as a mixture thereof.

In the present invention, it is preferred that emulsifiers not be used, because the use of the emulsifier may cause adverse effects such as changes in film solubilities on standing. However, emulsifiers such as sodium lauryl sulfate, polyoxyethylene nonyl phenylethers, polyoxyethylene sorbitanemonorate and polyoxysorbitane tristearate may be employed.

The dispersion of the solution of cellulose derivatives and water is subjected either by adding water to the solution or by adding the solution to water.

Means for dispersing the solution of cellulose derivatives with water in the presence of the alkali are usual emulsifying devices which produce stirring forces. Such devices include propeller stirrers, homogenizers, Mantongaulin type homogenizers, Nanomizer (Cosmo Keiso System Co., Ltd.) and Microfluidizer (MICROFUIDIC Inc.).

The enteric latex can be obtained by removing the organic solvent from the dispersion of cellulose derivatives and water. Part of water may be distilled from the latex to get the latex of the higher solids concentration. Removal of the organic solvent is usually carried out by distillation under normal or reduced pressures, steam stripping and airation. A vacuum emulsifying device such as T. K AGIHOMOMIXER (Tokushu Kika Industry Co., Ltd.) is advantageously applied when the solution of the cellulose derivatives is dispersed and emulsified with water in the presence of the alkali and the organic solvent is continuously removed.

When the organic solvent is removed, it is desirable that the aqueous dispersion of polymers is produced through a phase inversion in which a continuous phase containing the cellulose derivatives and the organic solvent is inverted to a dispersion phase; i.e., a phase inversion from a water-in-oil (w/o) type emulsion to an oil-in-water (o/w) type emulsion. It may be possible that the enteric latex is manufactured without changing the emulsion type from the O/W-type emulsion. In this case, however, water must be removed because too much water is present. On the other hand, in the method employing a phase inversion, the amount of removing water is minimum so that it is profitable in view of energy efficiency and productive efficiency requirements. It used to be very difficult to produce the stable enteric latex by removing the organic solvent accompanied by a phase inversion, because the emulsion is broken even if the emulsifier is optimized. In the present invention, however, the same procedures can be applied because the cellulose derivatives have self-emulsification properties.

It is essential to form the stable dispersion such that the diameter of dispersed solid particles in the enteric latex is no more than 20 $\mu$m. When it is greater than 20 $\mu$m, they precipitate with the passage of time. Generally, the smaller the size of the solid particles are, the better dispersion stabilities and film forming properties are. However, 0.1 $\mu$m is usually the smallest.

The shape of the dispersed solid particles is globular. In the present invention, the term "globular" doesn't mean indeterminate particles with edges which can be obtained by mechanical pulverization, but does mean almost globular fine particles with relatively smooth surfaces. It does not necessary mean genuine lobular particles. Due to globosity of the particles, the high dispersion stability can be obtained. Also, the good film forming properties can be obtained because filling properties of the particles present at the film forming are improved due to globosity of the particles.

The solids concentration of the enteric cellulose is between 5 and 40 weight %. If it is below 5 weight %, it is too dilute to be used practically. If it is more than 40 weight %, it is too viscous for its practical use because of difficulties encountered in its use during coating procedures.

The enteric latex of the present invention can be used as a film coating onto tablets and granules, with or without various additives like plasticizers. Any known coating apparatus such as pan coating apparatuses, film coating apparatuses like HI-COATER (Freund International Ltd.), fluidized coating apparatuses, agitating fluidized coating apparatuses can be employed.

DESCRIPTION OF PREFERRED EMBODIMENTS

The present invention will be illustrated in more detail with reference to the following non-limiting Examples, Applied Examples and Comparative Examples.

EXAMPLE 1

Forty (40) gram of carboxymethyl ethyl cellulose is dissolved in 360 gram of methyl acetate which is saturated by water. The solution is stirring at 8000 r.p.m. by a homogenizer for 5 minutes by adding 1.0 gram of the anti-foaming agent (Shin-Etsu Chemical Industry Co., Ltd. Silicone resin agent KM 72A) and 94 gram of water saturated by methyl acetate in which 1.22 gram of calcium hydroxide (53% of the carboxy methyl groups of carboxymethyl ethyl cellulose is neutralized by that amount of calcium hydroxide) is dispersed and dissolved. At this time, the continuous phase is a methyl acetate solution of carboxymethyl ethyl cellulose.

Then, methyl acetate is removed from the dispersion at 40° C. and 110 mm Hg vacuum by the rotary evaporator the continuous phase and the dispersion phase are inverted. The removal of methyl acetate is continued, then the stable polymer aqueous dispersion of 30% solids is obtained, in which globular fine particles of carboxymethyl ethyl cellulose are dispersed in water. The particle size is from 0.1 to 5 μm in diameter measured by the laser diffraction-type particle size analyzer. It takes about two hours to remove methyl acetate. The resulting dispersion (latex) is stable for two months at room temperature without any precipitation.

EXAMPLE 2

The same general procedure of Example 1 is followed for the preparation of the dispersion except that 94 gram of water with 1.44 gram of calcium hydroxide and 4 gram of cetanol is added. A stable polymer aqueous dispersion of 30% solids is obtained.

EXAMPLE 3

The same general procedure of Example 2 is followed for the preparation of the dispersion except that 0.5 gram of polyoxyethylene sorbitanmanorate is used in place of cetanol. A stable polymer aqueous dispersion is obtained.

EXAMPLE 4

The same general procedure of Example 1 is followed for the preparation of the dispersion except that 0.53 gram of magnesium hydroxide (41% of the carboxy methyl groups of carboxymethyl ethyl cellulose is neutralized by that amount of magnesium hydroxide) is dispersed in place of calcium hydroxide. A stable polymer aqueous dispersion is obtained.

EXAMPLE 5

The same general procedure of Example 1 is followed for the preparation of the dispersion except that 1.43 gram of barium hydroxide (30% of the carboxy methyl groups of carboxymethyl ethyl cellulose is neutralized by that amount of barium hydroxide) is dispersed in place of calcium hydroxide. A stable polymer aqueous dispersion is obtained.

EXAMPLE 6

The same general procedure of Example 1 is followed for the preparation of the dispersion except that 360 gram of methyl ethyl ketone which is saturated by water is used instead of methyl acetate. A stable polymer aqueous dispersion is obtained. The condition of the emulsion before the removal of the solvent is W/O-type.

EXAMPLE 7

The same general procedure of Example 1 is followed for the preparation of the dispersion except that 500 gram of water is used. A stable polymer aqueous dispersion is obtained. The condition of the emulsion before the removal of the solvent is O/W-type.

EXAMPLE 8

Four hundred (400) gram of carboxymethyl ethyl cellulose is dissolved in 1600 gram of methyl ethyl ketone which is saturated by water. 1.5 gram of calcium hydroxide (6% of the carboxy methyl groups of carboxymethyl ethyl cellulose is neutralized by that amount of calcium hydroxide) is dissolved in 933 gram of water saturated by methyl ethyl ketone. Then, this solution is added to the above polymer solution, and dispersed and emulsified for 5 minutes at 6000 r.p.m. of Homomixer-turbine and 75 r.p.m. of rotating paddle by the vacuum emulsification device (T. K. AGIHOMO-MIXER M-type, Tokushu Kika Industry Co., Ltd.). The continuous phase is a methyl ethyl ketone solution of carboxymethyl ethyl cellulose.

Then, methyl ethyl ketone is removed from the dispersion at 40° C. and 110 mm Hg vacuum, while the solution is stirring at 4000 r.p.m. of Homomixer-turbiune and 75 r.p.m. of rotating paddle. The continuous phase and the dispersion phase are inverted. The removal of methyl acetate is continued, then the stable polymer aqueous dispersion of 30% solids is obtained, in which globular fine particles of carboxymethyl ethyl cellulose are dispersed in water. The particle size is from 0.1 to 2 μm in diameter measured by the method of Example 1. It takes about three hours to remove methyl ethyl ketone. The resulting dispersion (latex) is stable for two months at room temperature without any precipitation.

Applied Example 1

To 460 gram of the latex of carboxymethyl ethyl cellulose obtained in Example 8, 41.4 gram of triethyl citrate is added, and then stirred for 30 minutes at 500 r.p.m. by a propeller stirrer. The resulting dispersion is coated onto 400 gram of placebo tablets in concentration of 8 weight % (32 gram as solids) by a film coating apparatus (HI-COATER HCT-MINI made by Freund International, Ltd.). Each of the tablets is composed of 30% of microcrystalline cellulose and 70% of lactose with a weight of 250 mg, a hardness of 10 Kg and a disintegration time is 10 seconds. The obtained film coated tablet is subjected to the disintegration test according to the 12th edition Japan pharmacopoeia. No disintegration is observed in the test with the first fluid (artificial gastric juice) and disintegration is observed in 4.4 minutes in the test with the second fluid (artificial intestinal juice). These results pass the test for enteric pharmaceutical tablets.

Comparative Example 1

The same general procedure of Example 1 is followed for the preparation of the dispersion except that calcium hydroxide is not used. An aqueous phase is separated and a stable polymer aqueous dispersion cannot be obtained.

Comparative Example 2

The same general procedure of Example 1 is followed for the preparation of the dispersion except that 1.51 gram of calcium hydroxide (65% of the carboxy methyl groups of carboxymethyl ethyl cellulose is neutralized by that amount of calcium hydroxide) is used in place of 1.22 gram of calcium hydroxide. The resulting solution is a white gel and a stable polymer aqueous dispersion cannot be obtained.

Comparative Example 3

The same general procedure of Example 3 is followed for the preparation of the dispersion except that calcium hydroxide is not used. An aqueous phase is separated and a stable polymer aqueous dispersion cannot be obtained.

Comparative Example 4

The same general procedure of Example 1 is followed for the preparation of the dispersion except that 1.14 gram of sodium hydroxide (45% of the carboxy methyl groups of carboxymethyl ethyl cellulose is neutralized by that amount of sodium hydroxide) is used in place of 1.22 gram of calcium hydroxide. The obtained dispersion becomes a gel after one month at room temperature, and a stable polymer aqueous dispersion cannot be obtained.

Comparative Example 5

The same general procedure of Example 1 is followed for the preparation of the dispersion except that ethanol, which is the hydrophilic solvent, is used in place of methyl acetate. A stable polymer aqueous dispersion cannot be obtained.

What is claimed is:

1. A latex of enteric polymers, which comprises:
   i) water and
   ii) enteric cellulose derivatives without ester-bonded substituents, the cellulose derivatives have anionic functional groups wherein from 0.5 to 60 mole % of the anionic functional groups are forming nontoxic salts with at least one cation selected from the group consisting of magnesium ion, calcium ion, barium ion and aluminum ion and the cellulose derivatives are globular solid particles With a diameter of 20 μm and below.

2. A latex of enteric polymers, which comprises:
   i) water,
   ii) enteric cellulose derivatives without ester-bonded substituents, and
   iii) at least one additive selected from a plasticizer, an anti-foaming agent, a suspension agent and an emulsifier, the cellulose derivatives have anionic functional groups wherein from 0.5 to 60 mole % of the anionic functional groups is forming nontoxic salts with at least one cation selected from the group consisting of magnesium ion, calcium ion, barium ion and aluminum ion and the cellulose derivatives are globular solid particles with a diameter of 20 μm and below.

3. The latex according to claims 1 or 2, wherein the cellulose derivative is carboxymethylethyl cellulose.

4. The latex according to claim 2, wherein the emulsifier is not contained in the latex.

5. The latex according to claims 1 or 2, wherein concentration of solids of the cellulose derivatives is from 5 to 40% by weight based on the latex.

6. A method for producing a latex of enteric cellulose derivatives without ester-bonded substituents, which comprises the following steps of:
   i) dissolving the cellulose derivatives with anionic functional groups in an solvent which is substantially water immiscible to get a solution,
   ii) dispersing the solution with water in the presence of at least one alkali selected from the group consisting of magnesium hydroxide, calcium hydroxide, barium hydroxide and aluminum hydroxide to form nontoxic salts with from 0.5 to 60 mole % of the anionic functional groups of the cellulose derivatives to obtain a dispersion, and
   iii) removing the organic solvent from the dispersion.

7. The method according to claim 6, wherein the cellulose derivatives in the dispersion are globular solid particles with a diameter of 20 μm and below.

8. The method according to claim 6, wherein a continuous phase of the enteric cellulose derivatives and the organic solvent and a dispersion phase of water are inverted by removing the organic solvent from the dispersion.

9. The method according to claim 6, wherein the cellulose derivative is carboxymethylethy cellulose.

* * * * *